United States Patent
Schneider et al.

(10) Patent No.: US 6,676,818 B1
(45) Date of Patent: Jan. 13, 2004

(54) EXHAUST GAS PROBE

(75) Inventors: Jens Stefan Schneider, Anderson, SC (US); Detlef Heimann, Gerlingen (DE); Hans-Joerg Renz, Leinfeldeon-Echterdingen (DE); Harald Neumann, Vaihingen (DE); Bernd Schumann, Rutesheim (DE); Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/744,842

(22) PCT Filed: Jul. 27, 1999

(86) PCT No.: PCT/DE99/02295

§ 371 (c)(1),
(2), (4) Date: Mar. 27, 2001

(87) PCT Pub. No.: WO00/07006

PCT Pub. Date: Feb. 10, 2000

(30) Foreign Application Priority Data

Jul. 30, 1998 (DE) .......................................... 198 34 276

(51) Int. Cl.$^7$ ............................................. G01N 27/407
(52) U.S. Cl. ........................ 204/424; 204/408; 204/426; 204/427
(58) Field of Search ................. 204/421–429, 204/408

(56) References Cited

U.S. PATENT DOCUMENTS

| | | | | |
|---|---|---|---|---|
| 4,097,353 A | * | 6/1978 | Kishida et al. | |
| 4,209,377 A | | 6/1980 | Furutani et al. | |
| 4,610,741 A | | 9/1986 | Mase et al. | |
| 4,806,739 A | | 2/1989 | Kojima et al. | |
| 5,302,275 A | | 4/1994 | Dietz et al. | |
| 5,516,410 A | * | 5/1996 | Schneider et al. | |
| 5,522,979 A | * | 6/1996 | Tatumoto et al. | |
| 5,593,558 A | * | 1/1997 | Sugino et al. | |
| 5,773,894 A | * | 6/1998 | Friese et al. | |

FOREIGN PATENT DOCUMENTS

DE 44 39 883 6/1995

\* cited by examiner

Primary Examiner—T. Tung
(74) Attorney, Agent, or Firm—Kenyon & Kenyon

(57) ABSTRACT

For the reduction of internal stresses and formation of cracks caused thereby, an exhaust gas probe includes two measuring electrodes separated by a solid electrolyte layer made substantially of $ZrO_2$ and a circuit-board conductor layer for electrically heating the solid electrolyte layer. The circuit-board conductor layer is firmly connected to the solid electrolyte layer via a first sealingly sintered insulating layer made of an $Al_2O_3$-containing material. A pore-forming material is added to the $Al_2O_3$-containing material before sintering.

10 Claims, 1 Drawing Sheet ively produced when the aluminum oxide component of the material includes $\alpha$-Al$_2$O$_3$ to the extent of at least 80%.

EXHAUST GAS PROBE

FIELD OF THE INVENTION

The present invention relates to an exhaust gas probe.

BACKGROUND INFORMATION

Exhaust gas probes for motor vehicles are generally referred to as lambda probes. The function of these probes is to measure a stream of oxygen ions diffusing through a solid electrolyte layer between two measuring electrodes. ZrO$_2$ is used as the material for such a solid electrolyte layer. A heating element in the form of a thin circuit-board conductor layer is used for heating the solid electrolyte layer to a temperature of several hundred degrees centigrade.

Constructing the entire body of the exhaust gas probe of zirconium oxide has certain disadvantages, because it leads to high leakage currents between the measuring electrodes and the circuit-board conductor layer through migration of oxygen ions of the ZrO$_2$, whereby the service life of the circuit-board conductor and thereby that of the entire sensor are impaired. It has been proven favorable not to bring the circuit-board conductor into direct contact with the ZrO$_2$, but rather to provide a layer in between, containing principally Al$_2$O$_3$, in which no migration of oxygen ions occurs.

However, producing an exhaust gas probe by sintering together layers of ZrO$_2$ and Al$_2$O$_3$ presents difficulties, since the sintering temperatures as well as the shrinking rates during sintering are different for the two materials. This leads to poor repeatability of the results of the sintering process, and consequently to the possibility of producing scrap.

The differential shrinkage rates of zirconium oxide and aluminum oxide have the additional consequence that sensors having asymmetrical layer structures tend to bend, which makes incorporating them into a mount more difficult. In symmetrically constructed sensors, the different materials are under considerable pull or push stresses, which, in combination with the fluctuating temperatures to which the sensor is exposed during the course of its operational life, can result in tears in the ceramic layers and in chipping off of material.

U.S. Pat. No. 4,806,739, a plate-shaped ceramic heating element, which includes a laminate structure made of a basic substrate of ZrO$_2$, a layer of Al$_2$O$_3$ applied by screen-printing technique, a circuit-board conductor layer and an exterior protective layer of Al$_2$O$_3$, the Al$_2$O$_3$ layers being tightly sintered. To prevent arching of this heating element, it is recommended that the distorting effect of an aluminum oxide layer on one side of the basic substrate be compensated so that a corresponding layer of aluminum oxide is also provided on the other side of the basic substrate. In this heating element the materials used are subject to considerable stresses.

SUMMARY OF THE INVENTION

The exhaust gas probe according to the present invention is formed by providing a controlled porosity in the layers of aluminum oxide-containing material. Thus, its elasticity is increased, and the effective material stresses in the probe may be reduced to the extent required for the mechanical stability of the exhaust gas probe.

The requisite quantity of pore-forming material may depend on the manner in which the sintering process is conducted, the coarseness and chemical composition of the layers to be sintered, and the pore-forming material used. For a given combination of these materials, however, it is possible to ascertain a suitable proportion of pore-forming material experimentally.

A densely sintered layer containing Al$_2$O$_3$ may be reliably and reproducibly produced when the aluminum oxide component of the material includes $\alpha$-Al$_2$O$_3$ to the extent of at least 80%.

During the operation of the exhaust gas sensor, a leakage current flows between the circuit-board conductor layer and the measuring electrodes. In ZrO$_2$, this occurs due to the migration of oxygen ions. The tightly sintered layer of Al$_2$O$_3$-containing material prevents access of oxygen to the circuit-board conductor layer. A leakage current between the circuit-board conductor layer and one of the measuring electrodes can, therefore, in ZrO$_2$, lead to an out-migration of oxygen, and consequently a blackening of the ZrO$_2$. To avoid this result, one tries to keep the leakage current as small as possible. For this purpose, the Al$_2$O$_3$-containing material should contain less than 50 ppm of sodium.

Finely divided carbon may be added to the Al$_2$O$_3$-containing material as pore-forming material, such as in the form of glassy carbon. The compactly formed particles of glassy carbon burn during the sintering process, and, as a result, leave compact, more or less spherical pores behind. In order to obtain closed pores, pore-forming materials having an average particle size of a maximum of 10 $\mu$m may be used, or an average particle size of the pore-forming material may be approximately 1 to 10 $\mu$m. Furthermore, the content of pore-forming material in the Al$_2$O$_3$-containing layers should not exceed 12% of the solids content of these layers.

Additionally, up to 10% ZrO$_2$ may be added to the Al$_2$O$_3$-containing material, for stress reduction.

In order to simplify sintering of the Al$_2$O$_3$-containing material, a fluxing agent may be added thereto, such as a fluxing agent containing fluorine. This may be in the form of the fluorine salt of an alkali or alkaline earth metal, such as a heavy metal such as barium, having ions that migrate in the sintered Al$_2$O$_3$-containing material only to a small extent, or in the form of ammonium fluoride or a fluoro-organic compound. Ammonia fluoride or a fluoro-organic compound may decompose during sintering, leaving only the flux-promoting fluorine behind in the Al$_2$O$_3$-containing material.

DETAILED DESCRIPTION

Figure 1:
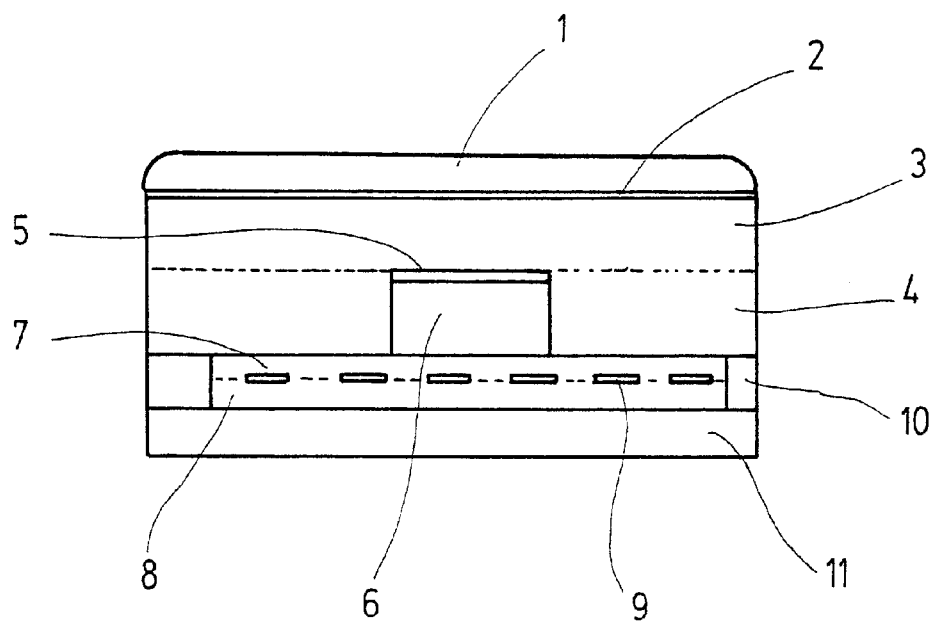
FIG. 1 is a schematic cross-sectional view of a first example embodiment of an exhaust gas probe according to the present invention.

The probe shown in FIG. 1 includes a porous protective layer 1, which comes into contact with the exhaust gas during the probe's operation, a Nernst electrode 2 lying below it, a solid electrolyte layer 3 between the Nernst electrode 2 and a reference electrode 5, a reference air duct foil 4, from which a reference air duct 6 has been formed below the reference electrode, two insulation layers 7, 8 above and below a circuit-board conductor layer 9, a sealing frame 10 enclosing the insulating layers 7, 8 sealingly towards the outside and a backing sheet 11. The electric leads of the circuit-board layer 9 are not illustrated in FIG. 1.

The solid electrolyte layer 3, the reference air duct foil 4 and the backing sheet 11 are produced by pouring foils from a suspension of $ZrO_2$ with a polymeric binding agent. After drying, the resulting foils may be processed further. These foils are cut to size, and, for the reference air duct foil, reference air duct 6 is stamped out.

One after another, insulating layer 8, circuit-board conductor layer 9 and then insulating layer 7 are applied to backing sheet 11, using a silk screen or spatula method. Insulating layers 7, 8 are made of substantially pure $\alpha$-$Al_2O_3$ (quality AKP53 of the firm Sumitomo) having a medium particle size of approximately 0.3 μm. A binding agent and a pore-forming material are further ingredients. Carbon, such as glassy carbon, having a particle size under 10 μm, in a proportion of up to 25% of the weight of the dried insulating layers, may be used as pore-forming material. Circuit-board conductor layer 9 is produced, for example, by silk screen printing of a suspension of spongy platinum onto insulating layer 8 in the form of a meander strip.

Solid electrolyte layer 3, with electrodes 2 and 5, reference air duct foil 4 and backing sheet 11 with insulating layers 7, 8 and circuit-board conductor layer 9 may then be laminated to form a stack, a sealing frame 10 being fitted all around the insulating layers 7, 8 which may be made substantially of $ZrO_2$, just as are solid electrolyte layer 3, reference air duct foil 4 and the backing sheet.

The prepared stack with protective layer 1 on top may then be heat treated. During this process, the polymeric binder of layers 3, 4, and 11 burns, and at a temperature of approximately 1000° C. the $ZrO_2$ begins to sinter. Sintering of the aluminum oxide occurs at approximately 1200° C. During the sintering and the cooling process, the $ZrO_2$-containing layers and the $Al_2O_3$-containing insulating layers may shrink to a different degree. The stress forces resulting from the differential shrinking may be reduced by the porosity of the insulating layers 7, 8 which results from the burning of the carbon during sintering. With a high carbon content of up to 25% in the material of the insulating layers, open pores may partially occur. In order to prevent gas exchange with the environment of the sensor via these pores, insulating layers 7, 8 may be surrounded all the way by a sealing frame 10 made of tightly sintered $ZrO_2$.

The appearance of arching in the exhaust gas probe of FIG. 1 is additionally avoided by surrounding the insulating layers 7, 8 on both sides by $ZrO_2$ layers, so that the effective stress forces on opposite sides of insulating layers 7, 8 compensate each other.

Figure 2:
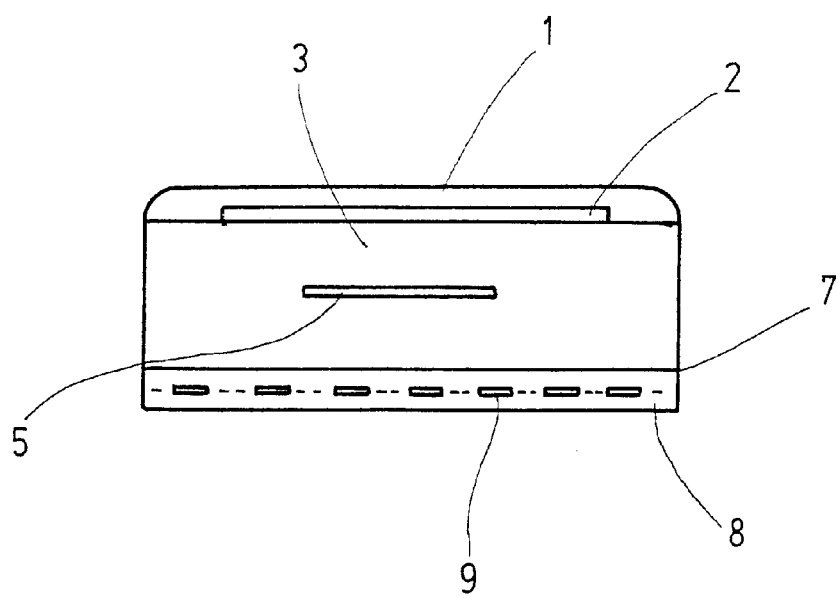
FIG. 2 is a schematic cross-sectional view of a second example embodiment of an exhaust gas probe according to the present invention.

FIG. 2 illustrates a second exemplary embodiment of the present invention, which has a simple construction. This embodiment differs from the embodiment illustrated in FIG. 1 in that backing sheet 11 and sealing frame 10 have been omitted, so that insulating layer 8 forms an open surface of the exhaust gas probe. In this exemplary embodiment, the content of glassy carbon in insulating layers 7 and 8, before sintering, is between 1 and 10%, preferably at 5% of the solids content of the $Al_2O_3$-containing insulating layers before sintering. Choosing a content of not more than 10% ensures that the pores formed during sintering remain closed, so that access of gas from the outside to circuit-board conductor layer 9 is effectively prevented. It is not necessary for durability reasons of the exhaust gas probe, to surround it with a sealing frame and a backing sheet made of tight $ZrO_2$. By using sufficiently pure $Al_2O_3$, as of the aforementioned type AKP53, it is possible to reduce leakage currents between circuit-board conductor layer 9 and electrodes 2, 5 to a value of approximately 1 μA. By comparison: When using another conventional type of aluminum oxide for producing exhaust gas probes, the one of quality CR85 from the firm of Baikowski (having 3% $SiO_2$ and 5% $BaCO_3$ as fluxing agent) in a correspondingly constructed exhaust gas probe, typically, leakage currents of 12–13 μA may occur. With these conventional, high leakage currents it was necessary to make possible access of fresh oxygen, e.g. from a reference air duct, to the circuit-board conductor layer, in order to prevent the leakage current, mediated by oxygen ion migration in the $ZrO_2$ layers from causing oxygen losses and thereby blackening of parts of the $ZrO_2$, which generally results in impairment of the service life of the exhaust gas probe. On the other hand, in the exhaust gas probe according to the present invention, the leakage currents are so low, that this oxygen access may not be necessary. Thus, in the present embodiment, the aluminum oxide of insulating layers 7, 8 may be and should be sintered to a sealing layer, which shuts off circuit-board conductor layer 9 from oxygen.

Such a sealingly sintered layer may be produced with aluminum oxide of the aforementioned type AKP53, which consists of up to more than 80% of $\alpha$-$Al_2O_3$. The fact that the $Al_2O_3$-containing layers of the present invention have a very low Na content of less than 50 ppm may contribute to the reduction of leakage current, whereas conventional layers may be contaminated with Na through the $BaCO_3$ portion, and as does also the fact that the layers according to the present invention may not contain a glass phase of $SiO_2$.

As a result, therefore, using sufficiently pure aluminum oxide, such as one low in sodium, and which is predominantly present in the form of $\alpha$-aluminum oxide, has the double advantage that it makes possible very low leakage currents between the circuit-board conductor layer and the measuring electrodes, so that, therefore, it is not necessary to pay attention to the possibility of oxygen access to circuit-board conductor layer 9, and that, therefore, circuit-board conductor layer 9 may be enclosed in sealingly sintered insulating layers 7, 8, which, in turn, are once produced from $\alpha$-aluminum oxide.

Since, in the embodiment illustrated in FIG. 2, the backing sheet made of $ZrO_2$ has been omitted, differential shrinkage rates of the $ZrO_2$-containing layers and the $Al_2O_3$-containing layers may occur and could lead to a residual arching of the finished probe, at sintering, and in spite of the porosity of the layers. This problem can be counteracted in various ways. A first solution is to sinter insulating layers 7, 8 from a mixture containing $Al_2O_3$ and up to 10% $ZrO_2$. This leads to sintering behavior of the different layers becoming more similar.

A second solution is to form insulating layers 7, 8 of aluminum oxide, such as the aforementioned aluminum oxide AKP53, and adding to it a fluxing agent, e.g. 0.1 to 0.5% LiF (lithium fluoride), approximately 0.1% $BaF_2$ (barium fluoride), $NH_4F$ (ammonium fluoride) or organically bound fluorine, such as, a fluoramine.

Sintering tests were performed on $Al_2O_3$ layers printed on a foil of polymer-bonded $ZrO_2$ and having an additive of lithium fluoride or barium fluoride as fluxing agent, at concentrations enumerated above. These tests did not show the arching typical of tests made without the addition of fluxing agents.

An exhaust gas sensor of the structure illustrated in FIG. 2 was produced for insulating layers 7, 8, using aluminum oxide laced with barium fluoride. This showed that the addition of barium fluoride did not result in an increase in the leakage current. On the average, a leakage current of 1 μA was measured.

Barium fluoride may be preferred among the alkali and alkaline earth fluorides as fluxing agent, since its relatively large and heavy ions have a low mobility in the insulating layers, and therefore do not contribute a considerable leakage current. Using ammonium fluoride or organic fluorine compounds as fluxing agent may also be effective, since these do not leave behind any ions in the insulating layer during sintering.

Using fluxing agents in, or adding $ZrO_2$ to insulating layers 7, 8 may, of course, be effective also in the embodiment illustrated in FIG. 1 for reducing internal stresses.

What is claimed is:

1. An exhaust gas probe, comprising:
   a measuring electrode;
   a reference electrode;
   a solid electrolyte layer separating the electrodes, the solid electrolyte layer being formed substantially of $ZrO_2$;
   a first sealingly sintered layer formed of an $Al_2O_3$-containing material, the $Al_2O_3$-containing material containing less than 50 ppm of sodium, the first sealingly sintered layer including pores, wherein the pores are formed by a pore-forming material added to the $Al_2O_3$-containing material before sintering and wherein the pore-forming material is not present after the sintering; and
   a circuit-board conductor layer configured to electrically heat the solid electrolyte layer, the circuit-board conductor layer being firmly connected to the solid electrolyte layer via the first sealingly sintered layer.

2. The exhaust gas probe according to claim 1, wherein an average particle size of the $Al_2O_3$-containing material is approximately 0.3 $\mu$m.

3. The exhaust gas probe according to claim 2, wherein the pore-forming material includes finely divided carbon.

4. The exhaust gas probe according to claim 3, wherein the finely divided carbon includes glassy carbon.

5. The exhaust gas probe according to claim 4, further comprising:
   a second sealingly sintered layer made of the $Al_2O_3$-containing material, wherein the first and second sealingly sintered layers have a carbon content up to 10% on a mass basis of the first and second sealingly sintered layers, wherein the carbon content as recited is only present prior to sintering.

6. The exhaust gas probe according to claim 1, wherein an average particle size of the pore-forming material is approximately 1 to 10 $\mu$m.

7. The exhaust gas probe according to claim 1, wherein the $Al_2O_3$-containing material includes up to 10% of $ZrO_2$.

8. The exhaust gas probe according to claim 1, wherein the $Al_2O_3$-containing material includes a fluxing agent, wherein the fluxing agent as recited is only present prior to sintering.

9. The exhaust gas probe according to claim 8, wherein the fluxing agent includes one of barium fluoride, lithium fluoride, ammonium fluoride, and an organically bound fluorine.

10. An exhaust gas probe, comprising:
    a measuring electrode;
    a reference electrode;
    a solid electrolyte layer separating the electrodes, the solid electrolyte layer being formed substantially of $ZrO_2$;
    a first layer formed of an $Al_2O_3$-containing material, the $Al_2O_3$ of the $Al_2O_3$-containing material includes, in an unsintered condition, at least 80% $\alpha$-$Al_2O_3$, the $Al_2O_3$-containing material containing less than 50 ppm of sodium, the first layer including a pore forming material;
    a circuit-board conductor layer configured to electrically heat the solid electrolyte layer, the circuit-board conductor layer being firmly connected to the solid electrolyte layer via the first layer.

* * * * *